United States Patent

Nagawa et al.

Patent Number: 4,959,479
Date of Patent: Sep. 25, 1990

[54] INDOLE DERIVATIVES

[75] Inventors: Yoshinobu Nagawa; Koichi Honda, both of Tsukuba; Hiroshi Nakanishi, Tsuchiura, all of Japan

[73] Assignee: Agency of Industrial Science & Technology, Tokyo, Japan

[21] Appl. No.: 426,648

[22] Filed: Oct. 26, 1989

Related U.S. Application Data

[62] Division of Ser. No. 237,465, Aug. 29, 1988, Pat. No. 4,889,937.

[30] Foreign Application Priority Data

Sep. 16, 1987 [JP] Japan .................... 62-231391

[51] Int. Cl.$^5$ .................. C07D 249/06; C07D 403/02
[52] U.S. Cl. ..................................... 548/255; 548/427
[58] Field of Search ................. 548/427, 255

[56] References Cited

U.S. PATENT DOCUMENTS 3,845,073 10/1974 Newberry ........................... 548/427

OTHER PUBLICATIONS

Honda, K. et al. "Syntheses and Spectroscopic Studies of 1,8-Bistriazolylnaphthalenes", *Journal of Chemical Society, Chemical Communications*, 1984, pp. 450–451.
Nagawa, Y. et al., "Synthesis and Reactivity of 1-(-8-Amino-1-naphthyl)-1H-1,2,3-triazoles", *Journal of Snythetic Organic Chemistry*, No. 10 (1987) pp. 905–906.
Nagawa, Y. et al, "Synthesis and Spectroscopic Studies of 1,1'-(1,8-Naphthylene)-di-1H-1,2,3-triazoles", *Bulletin of the Chemical Society of Japan*, vol. 60 (1987), pp. 2931–2935.

*Primary Examiner*—Glennon H. Hollrah
*Assistant Examiner*—Patricia L. Morris
*Attorney, Agent, or Firm*—Armstrong, Nikaido, Marmelstein, Kubovcik & Murray

[57] ABSTRACT

Disclosed are new indole derivatives of the following general formula (I):

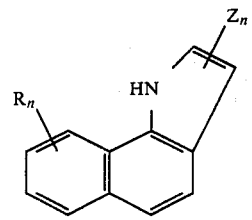

and a process for producing the derivatives (I) by irradiating a solution of a triazolylnaphthalene derivative of the following general formula (II) in a solvent with light:

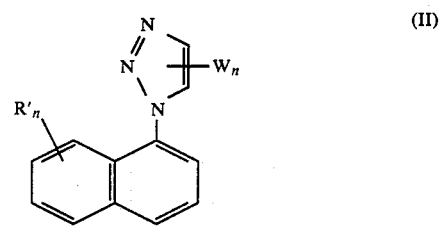

wherein R' represents a hydrogen atom, a halogen atom, an alkyl group, a nitro group or a

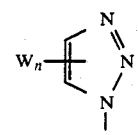

group, n represents a number of 1 or 2, and when n is 2, two R groups may be either the same or different from each other and $R_n$ is the same as $R'_n$ or represents a (Abstract continued on next page.)

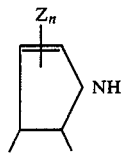
group ortho-condensed with the naphthalene ring: W and Z each represent a hydrogen atom, a halogen atom, an alkyl group, a carboxyl group or an ester group thereof, n represents a number of 1 or 2, and when n is 2, two W groups and two Z groups may be either the same or different from each other, respectively.
5 Claims, 1 Drawing Sheet

INDOLE DERIVATIVES

This application is a divisional of application Ser. No. 237,465, filed Aug. 29, 1988, now U.S. Pat. No. 4,889,937.

BACKGROUND OF THE INVENTION

The present invention relates to indole derivatives and a process for producing them. In particular, the present invention relates to new indole derivatives of which the pyrrole ring and the benzene ring have various substituents and a process for producing them by a photo-reaction.

The photo-reactions of triazoles are scarcely known, much less the products of the photo-reactions have ever been recognized.

SUMMARY OF THE INVENTION

The inventors have found that when a triazolylnaphthalene derivative is irradiated with light, the triazole ring releases its nitrogen atoms and an intramolecular condensation with the naphthalene ring occurs to form an indole derivative. The present invention has been completed on the basis of this finding.

Thus an object of the present invention is to provide new indole derivatives.

Another object of the present invention is to provide a process for producing indole derivatives by irradiating triazolylnaphthalene derivatives with light.

Still another object of the present invention is to provide indole derivatives usable as medicines, pesticides and industrial chemicals or as intermediates for them and a process for producing them.

THE PREFERRED EMBODIMENTS OF THE INVENTION

Figure 1:
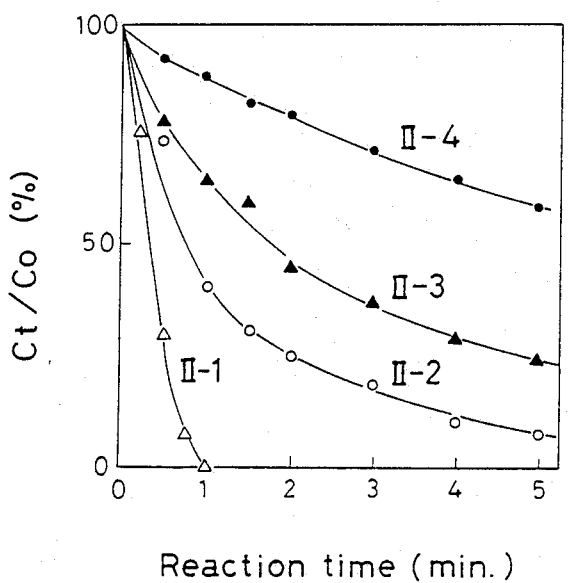
FIG. 1 shows the reaction rates of triazolylnaphthalene derivatives used as starting compounds for the new indole derivatives of the present invention.

The new indole derivatives of the present invention are represented by the following general formula (I):

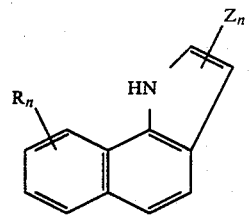

(I)

wherein R represents a hydrogen atom, an alkyl group, a halogen atom, an amino group, a nitro group a

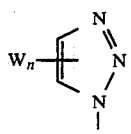

group or a group ortho-condensed with the naphthalene ring, n represents a number of 1 or 2, and when n is 2, two R groups may be either the same or different from each other;

W and Z each represent a hydrogen atom, a halogen atom, an alkyl group, a carboxyl group or an ester group thereof, n represents a number of 1 or 2, and when n is 2, two W groups and two Z groups may be either the same or different from each other, respectively.

The new indole derivatives of the present invention include, for example, compounds of the following structural formulae:

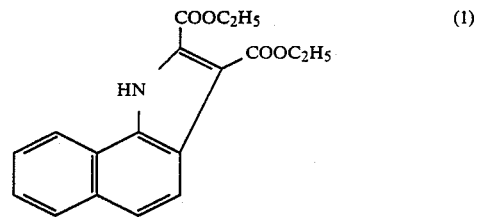

diethyl 1H-benz[g]indole-2,3-dicarboxylate,

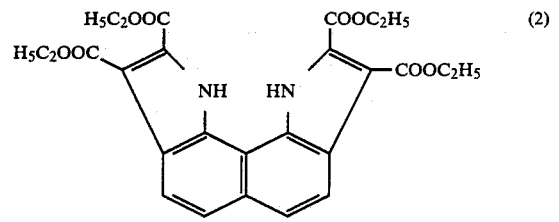

tetraethyl 1H,10H-indolo[6,7-g]indole-2,3,8,9-tetracarboxylate,

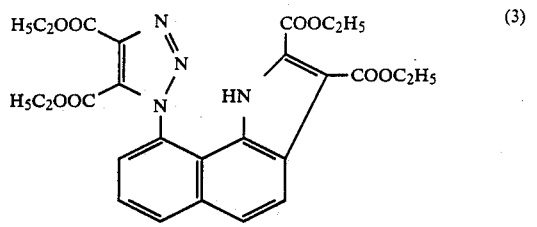

diethyl 9-(4,5-diethoxycarbonyl-1H-1,2,3-triazol-1-yl)-1H-benz[g]indole-2,3-dicarboxylate, (4)

9-methyl-1H-benz[g]indole,

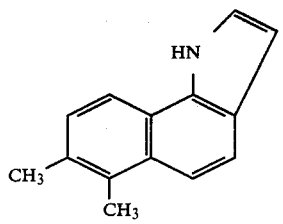

6,7-dimethyl-1H-benz[g]indole,

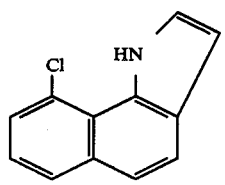

9-chloro-1H-benz[g]indole,

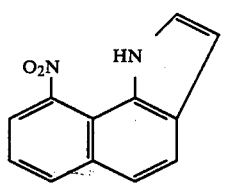

9-nitro-1H-benz[g]indole,

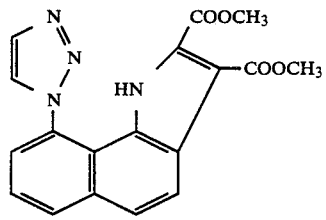

dimethyl 9-(1H-1,2,3-triazol-1-yl)-1H-benz[g]indole-2,3-dicarboxylate,

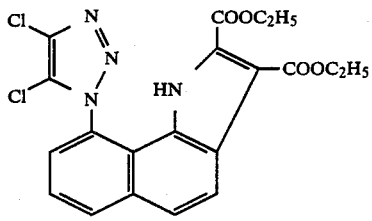

diethyl 9-(1H-1,2,3-triazol-1-yl)-1H-benz[g]indole-2,3-dicarboxylate,

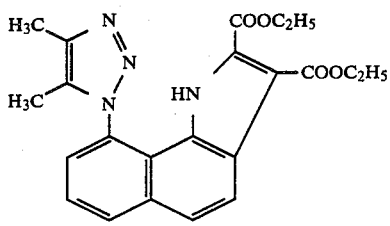

diethyl 9-(4,5-dimethyl-1H-1,2,3-triazol-1-yl)-1H-benz[g]indole-2,3-dicarboxylate,

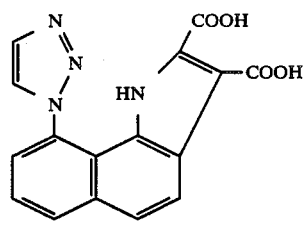

9-(1H-1,2,3-triazol-1-yl)-1H-benz[g]indole-2,3-triacarboxylate acid,

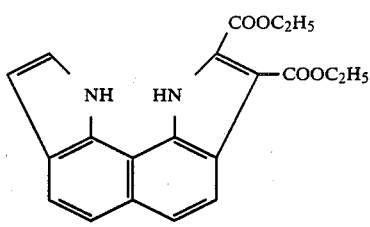

diethyl 1H,10H-indolo[6,7-g]indole-2,3-dicarboxylate,

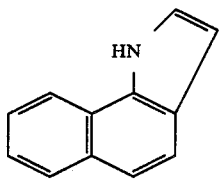

1H-benz[g]indole,

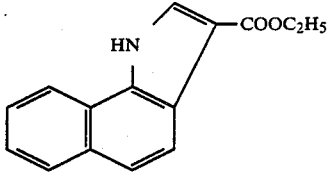

ethyl 1H-benz[g]indole-3-carboxylate,

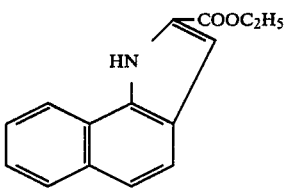

ethyl 1H-benz[g]indole-2-carboxylate,

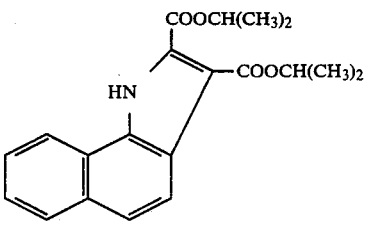

diisopropyl 1H-benz[g]indole-2,3-dicarboxylate,

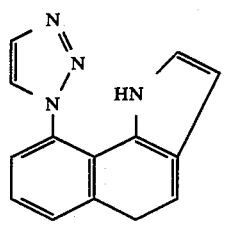

9-(1H-1,2,3-triazol-1-yl)-1H-benz[g]indole,

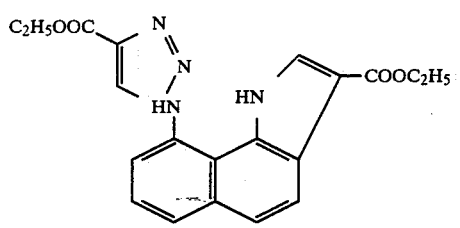

ethyl 9-(5-ethoxycarbonyl-1H-1,2,3-triazol-1-yl)-1H-benz[g]indole-3-carboxylate,

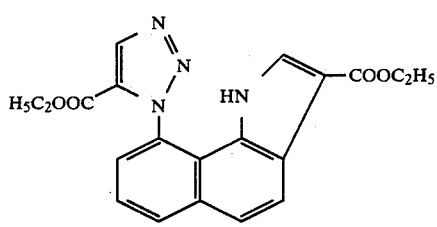

9-(5-ethoxycarbonyl-1H-1,2,3-triazol-1-yl)-1H-benz[g]indole-3-carboxylate,

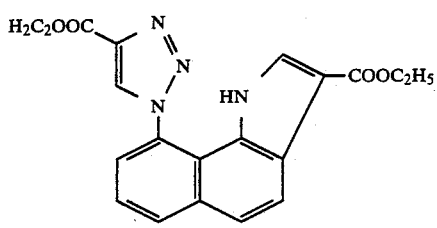

9-(4-ethoxycarbonyl-1H-1,2,3-triazol-1-yl)-1H-benz[g]indole-2-carboxylate,

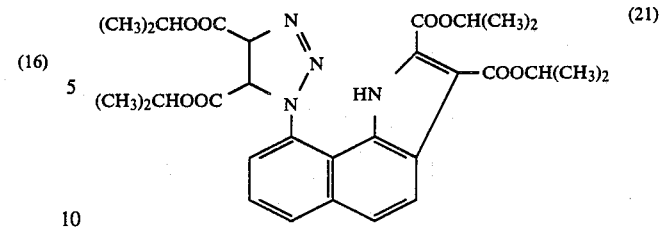

diisopropyl 9-(4,5-diisopropoxycarbonyl-1H-1,2,3-triazol-1-yl)-1H-benz[g]indole-2,3-dicarboxylate,

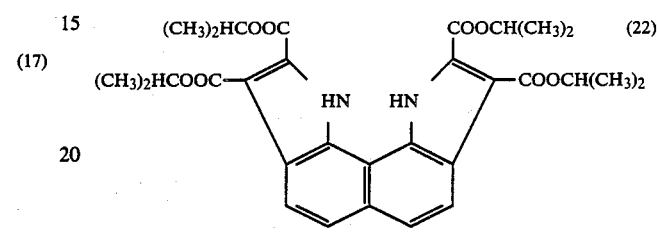

tetraisopropyl 1H,10H-indolo[6,7-g]indole-2,3,8,9-tetracarboxylate, and

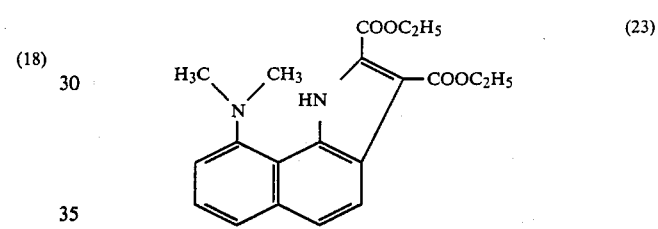

diethyl 8-dimethylamino-1H-benz[g]indole-2,3-dicarboxylate.

The new indole derivatives (I) of the present invention are produced by irradiating triazolylnaphthalene derivatives of the following general formula (II) with light:

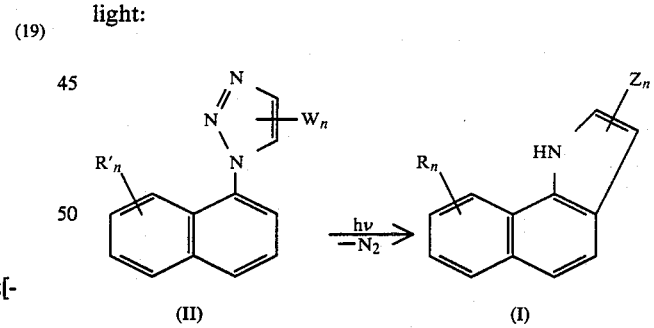

wherein R' represents a hydrogen atom, a halogen atom, an alkyl group, a nitro group or a

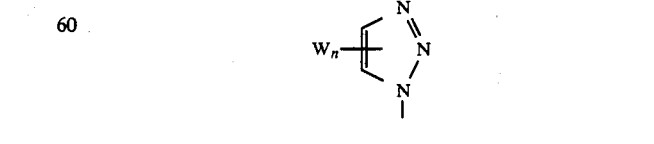

group, n represents a number of 1 or 2, and when n is 2, two R groups may be either the same or different from each other and $R_n$ is the same as $R'_n$ or represents a

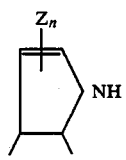

group ortho-condensed with the naphthalene group: W and Z each represent a hydrogen atom, a halogen atom, an alkyl group, a carboxyl group or an ester group thereof, n represents a number of 1 or 2, and when n is 2, two W groups and two Z groups may be either the same or different from each other, respectively.

The halogen atoms include chlorine, bromine, iodine and fluorine atoms.

The alkyl groups include those of a wide range, among which those having 1 to 5 carbon atoms, such as methyl, ethyl, propyl and butyl groups are preferred.

The esters of the COOH group are preferably those with the above-mentioned alkyl groups having 1 to 5 carbon atoms.

The triazolylnaphthalene derivatives used as the starting compound, such as 1,1'-(1,8-naphthylene)-di-1H-1,2,3-triazoles (II') and 1-(1-naphthyl)-1H-1,2,3-triazoles (II'') are prepared by reacting azidonaphthalene (IV) prepared from naphthaleneamine (III) with an acetylenecarboxylic acid derivative (V) as shown by the following reaction scheme:

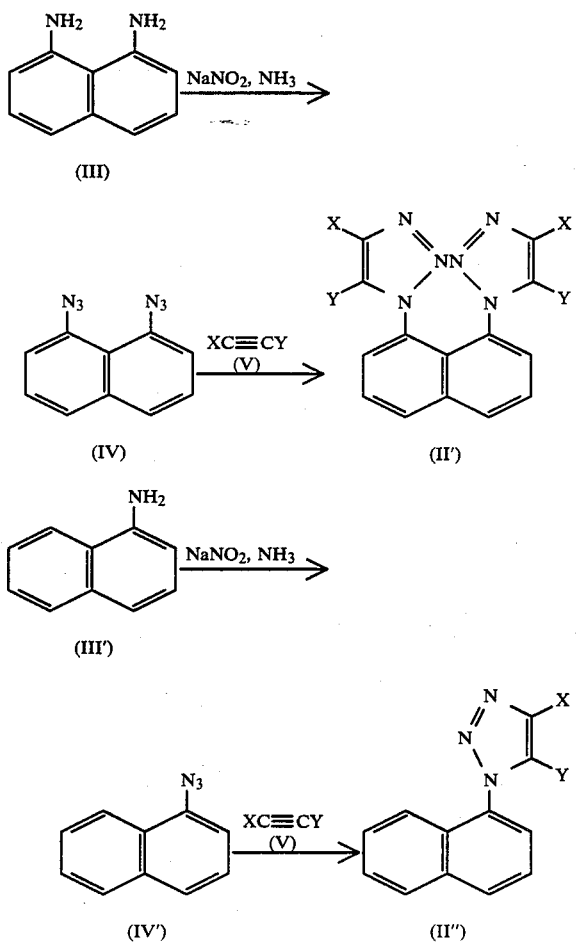

In the process for producing indole derivatives of the present invention, the irradiation of the starting compound (II) is conducted by dissolving it in a solvent, placing the solution thus obtained in a light radiation vessel and irradiating it with light for a specified time.

The solvent may be any one so far as the starting compound is soluble therein. The solvents include water, organic solvents and mixtures of them. Preferred examples include alcohols such as methanol and ethanol, ketones such as acetone, and ethers.

The light sources include those ordinarily used for the photo-reactions, such as high-pressure mercury lamps, ultraviolet lamps, halogen lamps and luminescent lamps. Since the starting triazolylnaphthalene derivative has a $\lambda_{max}$ at 280 to 290 nm, a light source that emits light within this wavelength range is preferably used. Though the irradiation may be conducted in the open air, it is conducted preferably in an inert gas atmosphere such as a nitrogen atmosphere.

The irradiation time ranges from 2 min to 1.5 h and the reaction temperature ranges from 20° C. to 40° C. The reaction is conducted usually under stirring.

After the completion of the photo-reaction, the solvent, etc. are removed in an ordinary manner and the product is purified by, for example, chromatography to yield the intended compound.

The use of the new indole derivatives of the present invention thus obtained as medicines, pesticides and industrial chemicals is expected. They are useful also as intermediates for these products.

The following examples will further illustrate the present invention.

EXAMPLE 1

Preparation of a Compound of the Structural Formula (1)

A starting compound of the above formula (II) wherein $R'_n$ is H and $W_n$ is $(-COOC_2H_5)_2$, i.e., diethyl 1-(1-naphthyl)-1H-1,2,3-triazole-4,5-dicarboxylate of the following structural formula (II-1), was used as the starting compound:

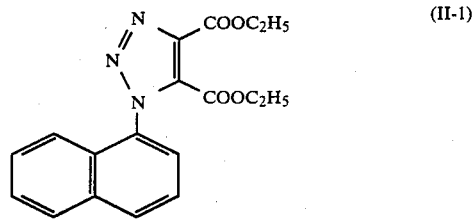

A 0.25 mM solution of the starting compound (II-1) in methanol was prepared. 400 ml of the solution was placed in a quartz internal irradiation tube and irradiated with a 500 W high-pressure mercury lamp in a nitrogen atmosphere for 2 min.

After the completion of the irradiation, methanol was distilled off under reduced pressure and the product was isolated by silica gel column chromatography to give diethyl 1H-benz[g]indole-2,3-dicarboxylate (3a). Yield: 90%. The reaction path is supposed to be as follows ($X=Y=-COOC_2H_5$):

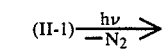

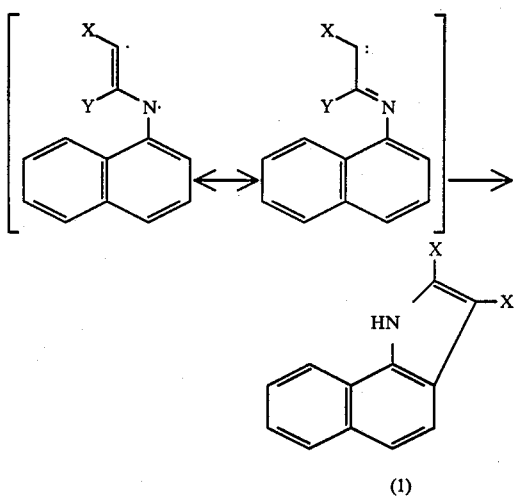

After the irradiation for 15 min, the formation of the Compound (1) was recognized.

The physical properties of the Compound (1) are shown in Table 1 given below together with those of a compound obtained in the following Example 2.

EXAMPLE 2

Preparation of Compounds of the Structural Formulae (2) and (3)

The same procedure as that of Example 1 was repeated except that a starting compound of the above formula (II) wherein W is —COOC$_2$H$_5$, R′$_n$ is

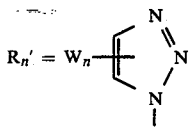

and n is 2, i.e. tetraethyl 1,1′-(1,8-naphthylene)di-1H-1,2,3-triazole-4,5-dicarboxylate of the following structural formula (II-2), was used as the starting compound:

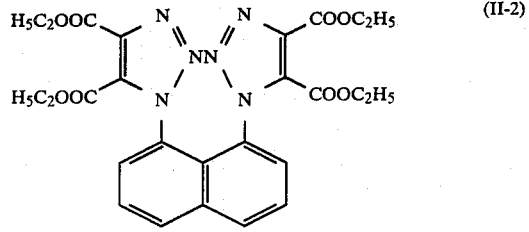

to give the compounds of the structural formulae (2) and (3), i.e. tetraethyl 1H,10H-indolo[6,7-g]indole-2,3,8,9-tetracarboxylate and diethyl 9-(4,5-diethoxycarbonyl-1H-1,2,3-triazol-1-yl)-1H-benz[g]-indole-2,3-dicarboxylate, respectively. The irradiation time was 2 min. Yields of the compounds of the structural formulae (2) and (3) were both 40%.

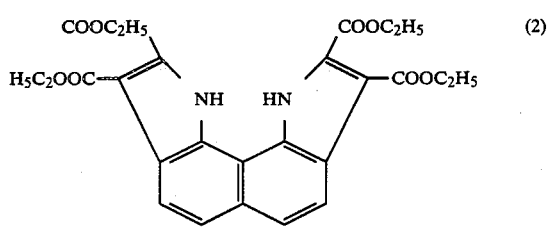

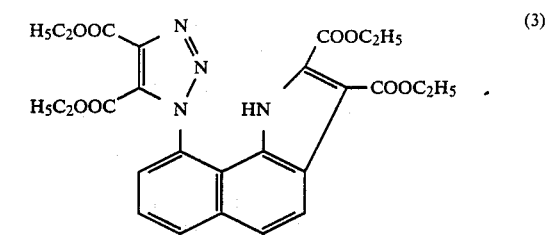

The physical properties of the Compounds (2) and (3) thus obtained are shown in Table 1 together with those of the Compound (1) obtained in Example 1.

It was found that in this step, the Lactam (13) was formed in addition to the Compounds (2) and (3).

Supposedly the Lactam (13) was formed by an intramolecular reaction via a compound of a keteneimine type (not separated) according to the following reaction path:

TABLE 1

| Structural formula | $^1$HNMR (CDCl$_3$, 20 mM) δ (ppm, TMS) | | | | | | | | IR (CCl$_4$, 2 mM) | UV (CH$_3$OH) |
|---|---|---|---|---|---|---|---|---|---|---|
| | NH | H4 | H5 | H6 | H7 | H8 | H9 | CH3 CH2 | ν (cm$^{-1}$) | λ (nm) |
| (1) | 10.52 | 7.99 | 7.59 | 7.91 | 7.54 | 7.54 | 8.23 | 1.47 4.49 | 3448 | 348.7, 335.3 |
| | | | | | | | | 1.43 4.47 | 1732 | 274.9, 248.5 |
| | | | | | | | | | 1697 | 206.9 |
| (2) | 11.44 | 8.00 | 7.68 | 7.68 | 8.00 | — | — | 1.48 4.50 | 3351 | 375.5, 361.3 |
| | | | | | | | | 1.45 4.48 | 1730 | 278.3, 246.9 |
| | | | | | | | | | 1698 | 207.7 |
| (3) | 8.21 | 8.24 | 7.76 | 8.19 | 7.64 | 7.54 | — | 1.47 4.53 | 3446 | 351.9, 334.9 |
| | | | | | | | | 1.45 4.47 | 1746 | 278.1, 252.7 |
| | | | | | | | | 1.40 4.36 | 1708 | 209.9 |
| | | | | | | | | 0.83 4.07 | | |

(II-2) $\xrightarrow{h\nu}{-N_2}$

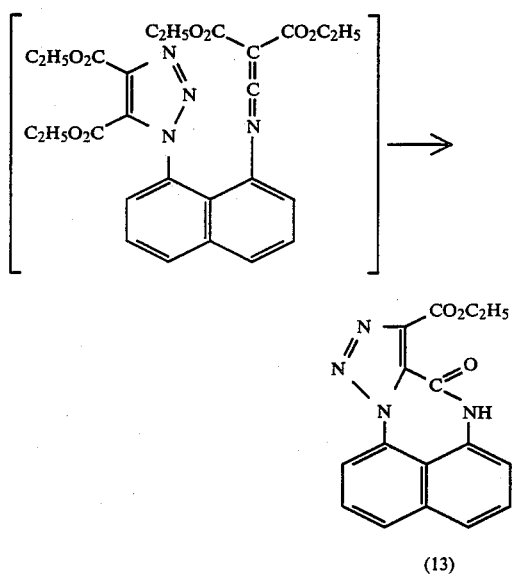

When the irradiation time was prolonged to 15 min, the Compound (2) was obtained in a yield of 70% and the formulation of the Lactam (13) was also recognized.

EXAMPLE 3

The same procedure as that of Example 1 was repeated except that a starting compound of the following formula (II) wherein $R'_n$ is H and $W_n$ is H, i.e. 1-(1-naphthyl)-1H-1,2,3-triazole of the following structural formula (II-3), was used as the starting compound to give 1H-benzo[g]indole (14).

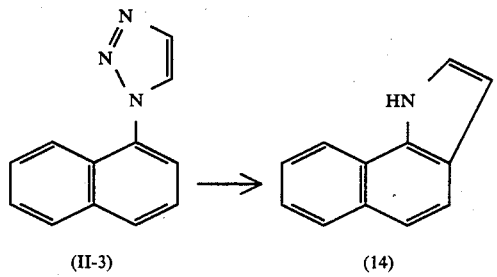

EXAMPLE 4

The starting compounds (II-1), (II-2) and (II-3) and a compound of the following structural formula (II-4) were irradiated with light in the same manner as that of Example 1 to examine the progress of the reaction under the same irradiation conditions. Namely, a reduction in the amount of each starting compound with time in the photo-reaction was traced by HPLC (reversed phase; ODS; methanol/water=90:10) to examine the reaction rate. The results are shown in FIG. 1. In FIG. 1, Co is the concentration of the starting compound in the initial stage and Ct is that after t min.

It is apparent from FIG. 1 that the reduction rate of the starting compound (II-1) was relatively high and that of (II-4) was low. This fact indicates that the reaction rate of the compound in which the triazole ring has an ethoxycarbonyl substituent is higher than that of the unsubstituted compound and that the reaction rate of the compound having two triazole rings is lower than that of the compound having one thiazole ring.

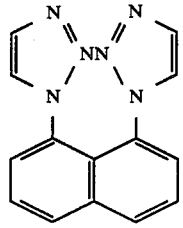

EXAMPLE 5

Various triazolylnaphthalene derivatives were irradiated with light by using the same irradiation apparatus as that of Example 1. The reaction results are shown in Table 2. The indole derivatives thus obtained were all new compounds.

In the reactions of forming the indole derivatives (13), (14), (15) and (16), substantially no change of the yield was recognized within the irradiation time of 2 to 20 min.

When the ester group was present at position 5 of the triazole ring of the starting triazolylnaphthalene derivative, the yield of the indole derivative formed was higher. In the reactions of forming the indole derivatives (17) to (20), no indolo[6,7-g]indole compounds were formed even when the irradiation time was prolonged. As the irradiation time was prolonged, the yield of the indole derivative was reduced. After the irradiation for 60 min, no indole derivative was detected at all.

Also in the reactions of forming the indole derivatives (21) and (22), the yield was reduced as the reaction time was prolonged.

In the reaction of forming the indole derivative (23), the reaction rate was relatively low and the yield was not increased even when the reaction time was prolonged.

TABLE 2

| Triazolylnaphthalene derivative | Structural formula No. of indole derivative formed | Irradiation time (min) | Yield (%) |
| --- | --- | --- | --- |
|  | 13 | 15 | 60 |

TABLE 2-continued

| Triazolylnaphthalene derivative | Structural formula No. of indole derivative formed | Irradiation time (min) | Yield (%) |
|---|---|---|---|
| [structure: 1-naphthyl-triazole-COOC$_2$H$_5$] | 14 | 15 | 60 |
| [structure: 1-naphthyl-triazole-COOC$_2$H$_5$ isomer] | 15 | 15 | 90 |
| [structure: 1-naphthyl-triazole-di-COOCH(CH$_3$)$_2$] | 16 | 15 | 90 |
| [structure: 1,8-bis(triazolyl)naphthalene] | 17 | 15 | 30 |
| [structure: 1,8-bis(triazolyl-COOC$_2$H$_5$)naphthalene] | 18 | 15 | 40 |
| [structure: 1,8-bis(triazolyl-COOC$_2$H$_5$)naphthalene isomer] | 19 / 20 | 15 / 15 | 20 / 20 |
| [structure: 1,8-bis(di-COOCH(CH$_3$)$_2$-triazolyl)naphthalene] | 21 / 22 | 2 | 30* / 40* |
| Same as above | 22 | 15 | 70* |

TABLE 2-continued

| Triazolylnaphthalene derivative | Structural formula No. of indole derivative formed | Irradiation time (min) | Yield (%) |
|---|---|---|---|
| 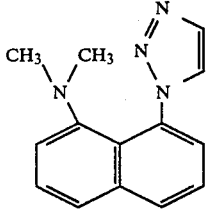 | 23 | 60 | 10 |

*The formation of Lactam (13) was observed like in Example 2.

We claim:

1. Indole derivatives of the following formula (I):

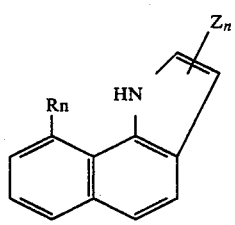
(I)

wherein R represents a Wn

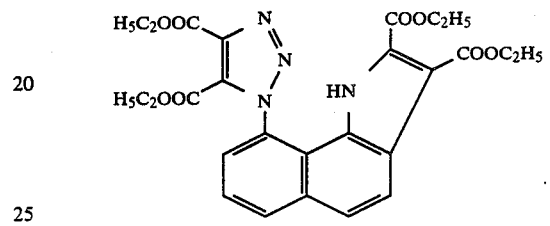

group or a R′nN-group, Z represents a hydrogen atom or a $C_1$–$C_5$ carboxylic acid alkyl ester group, W represents a hydrogen atom or a $C_1$–$C_5$ carboxylic acid alkyl ester group, R′ represents an $C_1$–$C_5$ alkyl group, and n in each instance above is the number 1 or 2.

2. Diethyl 9-(4,5-diethoxycarbonyl-1H-1,2,3-triazol-1-yl)-1H-benz[g]indole-2,3-dicarboxylate, of the formula:

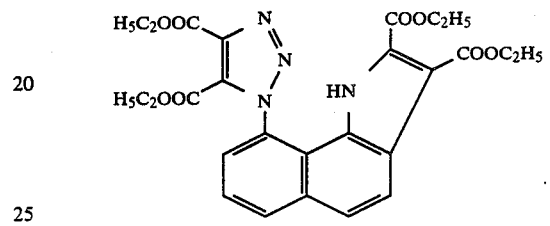

3. 9-(1H-1,2,3-triazol-1-yl)-1H-benz[g]indole, of the formula:

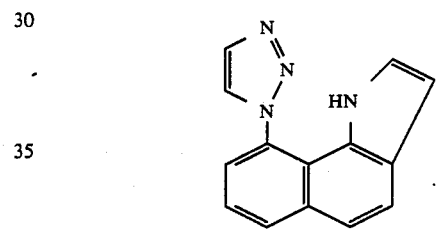

4. Diisopropyl 9-(4,5-diisopropoxycarbonyl-1H-1,2,3-triazol-1-yl)-1H-benz[g]indole-2,3-dicarboxylate, of the formula:

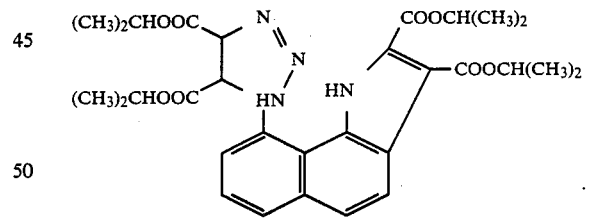

5. Diethyl 8-dimethylamino-1H-benz[g]indole-2,3-dicarboxylate, of the formula:

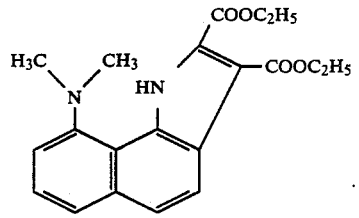

* * * * *